US008342013B2

(12) United States Patent
Nedachi et al.

(10) Patent No.: US 8,342,013 B2
(45) Date of Patent: Jan. 1, 2013

(54) OIL-DEGRADATION DETERMINATION APPARATUS

(75) Inventors: Yoshiaki Nedachi, Saitama (JP); Takashi Ozeki, Saitama (JP); Kousuke Tsunashima, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 633 days.

(21) Appl. No.: 12/364,065

(22) Filed: Feb. 2, 2009

(65) Prior Publication Data

US 2009/0217740 A1 Sep. 3, 2009

(30) Foreign Application Priority Data

Feb. 28, 2008 (JP) .................................. 2008-047761

(51) Int. Cl.
G01N 11/00 (2006.01)
(52) U.S. Cl. ..................... 73/114.55; 73/53.05; 73/54.01
(58) Field of Classification Search ................... 73/53.01, 73/54.01, 54.02, 53.05, 114.55
See application file for complete search history.

(56) References Cited

U.S. PATENT DOCUMENTS

| | | | | |
|---|---|---|---|---|
| 6,267,002 B1 * | 7/2001 | Ehwald et al. | ............... | 73/54.01 |
| 6,575,018 B2 * | 6/2003 | Berndorfer et al. | .......... | 73/54.01 |
| 6,640,617 B2 * | 11/2003 | Schob et al. | ................. | 73/54.01 |
| 7,275,419 B2 * | 10/2007 | Raffer | ........................... | 73/54.28 |
| 7,677,086 B2 * | 3/2010 | Albertson et al. | ........... | 73/54.02 |
| 7,690,246 B1 * | 4/2010 | Discenzo | ..................... | 73/53.05 |
| 2003/0005751 A1 | 1/2003 | Berndorfer et al. | | |
| 2003/0103852 A1 * | 6/2003 | Schob | ........................ | 417/410.1 |
| 2003/0172722 A1 * | 9/2003 | Jakoby | ......................... | 73/53.05 |
| 2003/0223879 A1 * | 12/2003 | Yanai et al. | ...................... | 417/43 |

FOREIGN PATENT DOCUMENTS

| | | |
|---|---|---|
| DE | 100 55 420 A1 | 5/2002 |
| JP | 03-026855 | 2/1991 |
| JP | 2003-524169 A | 8/2003 |

* cited by examiner

*Primary Examiner* — David Rogers
(74) *Attorney, Agent, or Firm* — Squire Sanders (US) LLP

(57) ABSTRACT

A method and apparatus for determining oil degradation measures a first electric-current value of a driving current used to operate an electric oil pump at a predetermined consistent revolution, and stores the first electric-current value as an electric-current initial value. Data is corrected by measuring a second electric-current value of the driving current, with the second electric-current value being measured when the electric pump is operated at the predetermined consistent revolution when the engine is driven a predetermined time after the electric-current initial value is stored. The electric-current initial value is compared with the second electric-current value. It is then determined that a viscosity of the oil has become low when a difference between the electric-current initial value and the second electric-current value is equal to or greater than a predetermined value.

7 Claims, 2 Drawing Sheets

OIL-DEGRADATION DETERMINATION APPARATUS

BACKGROUND OF THE INVENTION

1. Field of the Invention

The present invention relates to an apparatus for determining the degradation of oil circulated in and supplied to various parts of an engine. Especially, the present invention relates to an oil-degradation determination apparatus for determining the degradation of oil circulated in and supplied to the engine, on the basis of measured data on an electric pump used for circulating and supplying the oil, without using a sensor or the like to directly detect the viscosity or other parameters of the oil.

2. Description of the Related Art

Engine oil that is circulated and supplied to the cylinder-wall surfaces and the bearings of an engine mounted, for example, on an automobile or a motorcycle is gradually degraded as the vehicle travels. Accordingly, it has been conventionally recommended to change the oil to new one on the basis of either a travel distance or the period of its service.

Specifically, a common way of determining when to change the engine oil is to record a travel distance and to change the oil once the vehicle has traveled a predetermined distance on the basis of the recorded travel distance (a travel-distance integration method). Another way thereof is to always detect the condition of the engine oil by use of a sensor, and to change the oil when the degradation of the oil is observed by the sensor (detection-by-sensor method). More specifically, as Patent Document JP-A-3-26855 and Patent Document JP-T-2003-524169 describe, the condition of the engine oil is determined on the basis of physical properties of the oil, such as the viscosity and the non-permittivity of the oil, and the oil is changed when the oil is degraded.

SUMMARY OF THE INVENTION

An oil-degradation determination apparatus according to an embodiment of the invention can comprise an initial-value storing unit configured to measure a first electric-current value of a driving current used to operate an electric oil pump at a predetermined constant revolution. The electric pump is configured to circulate oil in an engine. The initial-value storing unit is also configured to store the first electric-current value as an electric-current initial value. A pump-driving-time date measurement unit is configured to correct data by measuring a second electric-current value of the driving current. The second electric-current value is measured when the electric pump is operated at the predetermined constant revolution when the engine is driven a predetermined time after the electric-current initial value is stored. A comparison unit is configured to compare the electric-current initial value with the second electric-current value. A determiner is configured to determine that a viscosity of the oil has become low when it is determined that a difference between the electric-current initial value and the second electric-current value is equal to or greater than a predetermined value.

An oil-degradation determination apparatus according to another embodiment of the invention can comprise an initial-value storing unit configured to measure a first revolution speed of an electric pump when the electric pump is operated with a predetermined constant electric current. The electric pump is configured to circulate oil in an engine. The initial-value storing unit also configured to store the first revolution speed as a revolution initial value. A pump-driving-time data measurement unit is configured to collect data by measuring a second revolution speed of the electric pump while the electric pump is operated with the predetermined constant electric current, when the engine has been driven a predetermined time after the storing of the revolution initial value. A comparison unit is configured to compare the revolution initial value with the second revolution speed. A determiner is configured to determine that a viscosity of the oil has become low when it is determined that a difference between the revolution initial value and the second revolution speed is equal to or greater than a predetermined value.

An oil-degradation determination apparatus, according to another embodiment of the invention can include an initial-value storing means for measuring a first electric-current value of a driving current used to operate an electric oil pump at a predetermined constant revolution. The electric pump circulates oil in an engine. The initial-value storing means also stores the first electric-current value as an electric-current initial value. A pump-driving-time date measurement means corrects data by measuring a second electric-current value of the driving current. The second electric-current value is measured when the electric pump is operated at the predetermined constant revolution when the engine is driven a predetermined time after the electric-current initial value is stored. A comparison means for comparing the electric-current initial value with the second electric-current value is provided. A determining means determines that a viscosity of the oil has become low when it is determined that a difference between the electric-current initial value and the second electric-current value is equal to or greater than a predetermined value.

An oil-degradation determination apparatus according to yet another embodiment of the invention can comprise an initial-value storing means for measuring a first revolution speed of an electric pump when the electric pump is operated with a predetermined constant electric current. The electric pump is for circulating oil in an engine. The initial-value storing means is also for storing the first revolution speed as a revolution initial value. A pump-driving-time data measurement means is provided for collecting data by measuring a second revolution speed of the electric pump while the electric pump is operated with the predetermined constant electric current, when the engine has been driven a predetermined time after the storing of the revolution initial value. A comparison means is provided for comparing the revolution initial value with the second revolution speed. A determining means is provided for determining that a viscosity of the oil has become low when it is determined that a difference between the revolution initial value and the second revolution speed is equal to or greater than a predetermined value.

A method of determining oil-degradation according to another embodiment of the invention includes measuring a first electric-current of a driving current used to operate an electric oil pump at a predetermined consistent revolution, the electric oil pump circulating oil in an engine. The first electric-current value is stored as an electric-current initial value. A second electric-current value of the driving current is provided when the electric pump is operated at the predetermined constant revolution when the engine is driven a predetermined time after the electric-current initial value is stored. The electric-current initial value is compared with the second electric-current value. A viscosity of the oil is determined to have become low when a difference between the electric-current initial value and the second electric-current value is equal to or greater than a predetermined value.

An oil-degradation determination apparatus according to another embodiment includes measuring a first revolution speed of an electric pump when the electric pump is operated with a predetermined consistent electric current, the electric pump circulating oil in an engine. The first revolution speed is stored as a revolution initial value. A second revolution speed of the electric pump is stored while the electric pump is operated with the predetermined consistent electric current when the engine has been driven a predetermined time after the storing of the revolution initial value. The revolution initial value is compared with the second revolution speed. A viscosity of the oil is determined to have become low when a difference between the revolution initial value and the second revolution speed is equal to or greater than a predetermined value.

DETAILED DESCRIPTION OF PREFERRED EMBODIMENTS

Figure 1:
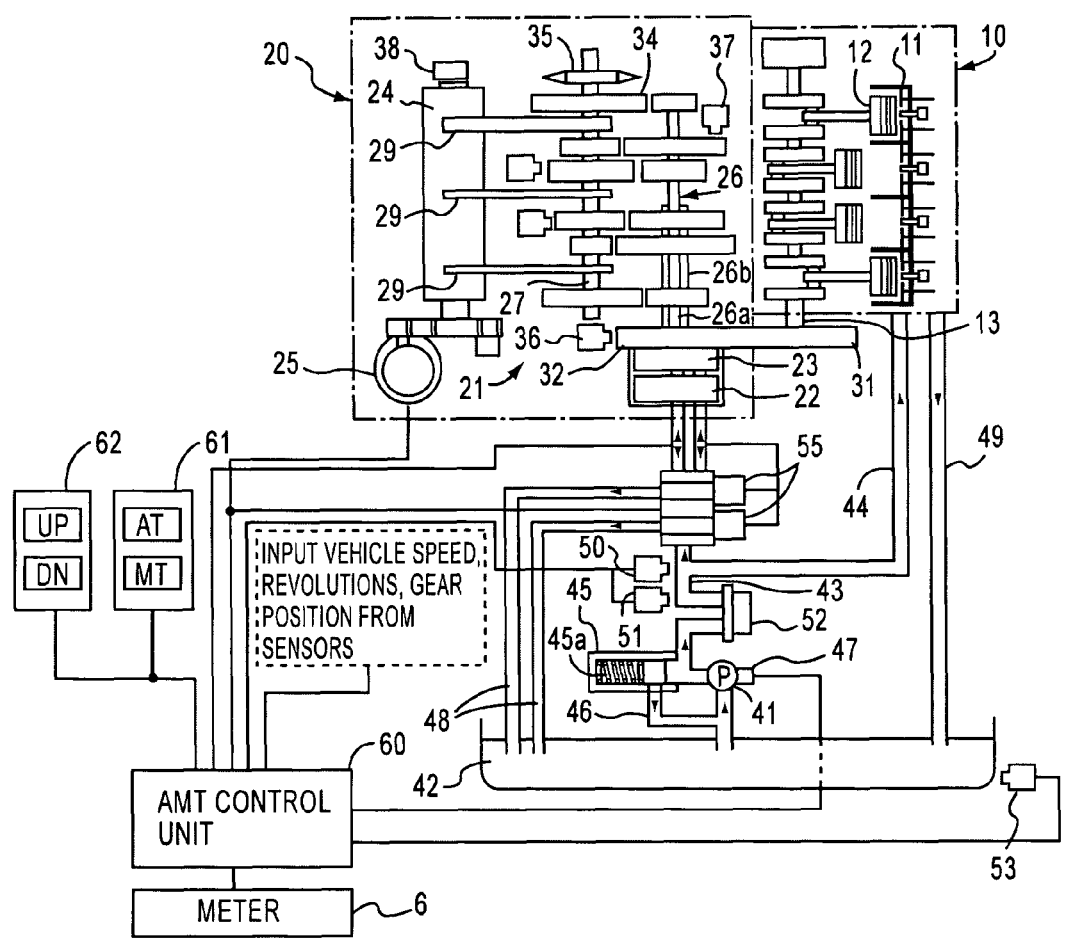
FIG. 1 is a system configuration diagram of a transmission control system that also serves as an oil-degradation determination apparatus according to an embodiment of the present invention.

The degradation of the engine oil largely depends on the driving mode, that is, the way of using the engine including the way where the vehicle often runs on a road in traffic jam, or where the engine often runs at a high speed, for example.

Because the driving mode is different depending on the user, the engine oil has to be changed well in advance in the above-mentioned travel-distance integration method.

When the engine oil is changed in the above-mentioned detection-by-sensor method, on the other hand, a sensor to detect the degradation of oil from the physical properties of the oil has to be placed at a position where the sensor can be in contact with the engine oil, thus resulting in a complex structure and a cost increase.

An embodiment of the present invention can provide an oil-degradation determination apparatus for detecting the degradation of oil that is circulated in and supplied to an engine, on the basis of measured data on an electric pump that circulates and supplies the oil, without using a special sensor to detect the degradation of the oil.

In one embodiment, the present invention provides an oil-degradation determination apparatus for determining the degradation of oil that is circulated in and supplied to an engine on the basis of measured data on an electric pump that circulates the oil in and supplies the oil to the engine. A first feature of the oil-degradation determination apparatus according to this example is to include initial-value storing unit, pump-driving-time data measurement unit, comparison unit, and determination unit.

The initial-value storing unit is configured to measure an electric-current value of a driving current used to operate the electric pump at a predetermined constant revolution, and to store the electric-current value as an electric-current initial value.

The pump-driving-time data measurement unit can be configured to collect data by measuring an electric-current value of a driving current used to operate the electric pump at the predetermined constant revolution when the engine is driven a predetermined time after the storing of the electric-current initial value.

The comparison unit is configured to compare the electric-current initial value with the electric-current value that is measured the predetermined time after the storing of the electric-current initial value.

The determination unit is configured to determine that the viscosity of the oil has become low. Such determination is made on condition that a difference between the two electric-current values compared by the comparison unit is equal to or more than a predetermined value.

Another embodiment of the present invention provides an oil-degradation determination apparatus for determining the degradation of oil that is circulated in and supplied to an engine on the basis of measured data on an electric pump that circulates the oil in and supplies the oil to the engine. A second feature of the oil-degradation determination apparatus according to embodiments of the present invention is to include an initial-value storing unit, pump-driving-time data measurement unit, a comparison unit, and a determination unit.

The initial-value storing unit can be configured to measure a revolution of the electric pump when the electric pump is operated with a predetermined constant electric current, and to store the revolution as a revolution initial value.

The pump-driving-time data measurement unit can be configured to collect data by measuring a revolution of the electric pump while the electric pump is operated with the predetermined constant electric current when the engine is driven a predetermined time after the storing of the revolution initial value;

The comparison unit can be configured to compare the revolution initial value with the revolution that is measured the predetermined time after the storing of the revolution initial value.

The determination unit can be configured to determine that the viscosity of the oil has become low. Such determination is done on condition that a difference between the two revolutions compared by the comparison unit is equal to or more than a predetermined value.

Another embodiment of the present invention can have a third feature to further include a warning device or warning means which is configured to perform at least one of showing a display and generating a sound, each indicating that the viscosity of the oil has become low, on condition that the determination unit determines that the viscosity of the oil has become low.

In another embodiment, the present invention has, in the oil-degradation determination apparatus a fourth feature in that the pump-driving-time data measurement unit collects the data at desired regular intervals.

In yet another embodiment, the present invention can have a data recording unit configured to record pieces of data measured at the regular intervals by the pump-driving-time data measurement unit; and an oil-change time calculating unit configured to calculate, from the pieces of data stored in the data recording unit, a time to change the oil.

The present invention can have in the oil-degradation determination apparatus, a further feature in that the electric-current initial value is measured and stored immediately after the changing of the oil.

The present invention can also have in the oil-degradation determination apparatus, an additional feature in that the revolution initial value is measured and stored immediately after the changing of the oil.

According to the present invention having some of the various features mentioned above, the oil-degradation determination apparatus determines the degraded state of the engine oil by comparing the electric-current initial value with the electric-current value of the driving current for the electric pump measured while the electric pump is constantly running at the predetermined revolution. Accordingly, the oil-degradation determination apparatus can appropriately determine when to change the oil, without relying on any special sensor.

According to embodiments the present invention having various of these features, the oil-degradation determination apparatus can determine the degraded state of the engine oil by comparing the revolution initial value with the revolution value of the electric pump measured while the electric pump is constantly running with the predetermined electric current. Accordingly, the oil-degradation determination apparatus can appropriately determine when to change the oil without relying on any special sensor.

According to other embodiments of the invention, the oil-degradation determination apparatus is provided with a warning device which either displays or sounds a warning in a case of determining that the viscosity of the oil has become low. Accordingly, the user can be notified of the degradation of the oil.

According to other embodiments of the invention, the pieces of data are measured at desired regular intervals. Accordingly, the degraded state of the oil can be determined for every predetermined time.

According to yet another embodiment, the oil-change time calculating means can calculate, from the pieces of data measured at regular intervals, when to change the oil. Accordingly, the user can be notified, in advance, of when to change the oil.

Figure 2:
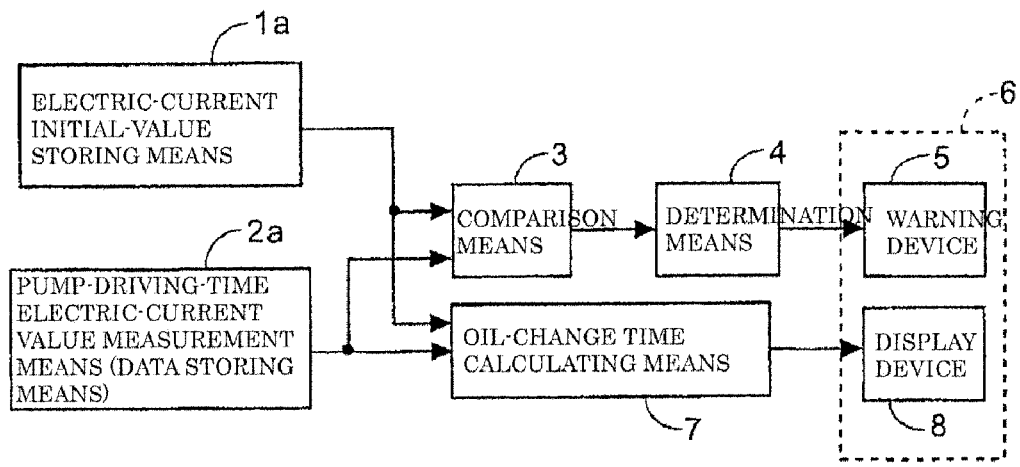
FIG. 2 is a general block diagram of the oil-degradation determination apparatus according to one embodiment of the present invention.

Various embodiments of the present invention will be described below with reference to the accompanying drawings. FIG. 1 is a system general configuration diagram of a motorcycle on which an oil-degradation determination apparatus of the present invention is mounted. FIG. 2 is a general block diagram of the oil-degradation determination apparatus according to the embodiment of the present invention. The oil-degradation determination apparatus shown in this embodiment is an apparatus for determining the degradation of oil that is circulated in and supplied to the engine of the motorcycle.

In FIG. 1, the motorcycle includes, for example, an automatic manual transmission (AMT) 20 that is joined to an engine 10, a hydraulic system 40 that controls the twin clutch of the AMT 20 as well as circulates and supplies oil to the engine 10, and an AMT control unit 60 that controls the AMT 20.

This example of the oil-degradation determination apparatus is configured to determine the degradation of oil by inputting measured data on the electric-current value and the revolutions of an electric pump 41 used for re-circulating and supplying oil of the hydraulic system 40.

The amount of oil supplied by an oil pump connected to and driven by the engine depends on the revolutions of the engine. In contrast, the electric pump 41 used in the hydraulic system 40 is capable of preventing oil from being supplied excessively even when the engine revolves at a high speed, and of keeping the amount of circulated engine oil at an appropriate level, since the amount of oil to be circulated and supplied can be controlled by the driving current of the electric pump 41.

The engine 10 includes a crankshaft 13 that is rotated by the reciprocating movement of multiple pistons 12 disposed in a cylinder block 11. A primary drive gear 31 is coupled to the crankshaft 13 which serves as the output shaft of the engine 10.

In one example, the AMT 20 is an automatic manual transmission equipped with a twin clutch. The AMT 20 includes multiple-speed transmission gears 21, a first clutch 22, a second clutch 23, a shift drum 24, and a shift control motor 25. Each of the multiple gears included in the transmission gears 21 is either coupled to or loosely fitted to the corresponding one of a main shaft 26, a counter shaft 27, and a transmission-gear output shaft 28. The main shaft 26 includes an inner main shaft 26a and an outer main shaft 26b. The first clutch 22 is coupled to the inner main shaft 26a while the second clutch 23 is coupled to the outer main shaft 26b.

Dog clutches (not illustrated) are provided respectively on the main shaft 26 and the counter shaft 27. The dog clutches thus provided are capable of being respectively displaced in the axial direction of the main shaft 26 and the counter shaft 27. Ends of each of shift forks 29 respectively engage with the dog clutch and a cam groove (not illustrated) formed in the shift drum 24.

The primary drive gear 31, coupled to the crank shaft 13 of the engine 10, meshes with a primary driven gear 32 of the AMT 20. The primary driven gear 32 is connected to the inner main shaft 26a via the first clutch 22, and is also connected to the outer main shaft 26b via the second clutch 23. The hydraulic system 40 controls the connection of the first clutch 22 and the second clutch 23 to either the inner main shaft 26a or the outer main shaft 26b.

A drive sprocket 35 is coupled to the counter shaft 27. The drive sprocket 35 is linked to a driven sprocket of the rear wheel of the motorcycle through a drive chain (not illustrated).

The AMT 20 can include an engine-revolution sensor 36 placed so as to face the outer circumference of the primary driven gear 32 and a vehicle-speed sensor 37 placed so as to face the outer circumference of the gear coupled to the inner main shaft 26a subjected to the primary reduction. A gear-position sensor 38 detects the shift position accomplished by the shift drum 24.

The hydraulic system 40 can include an oil tank 42 and a pipe 43 to feed the oil in the oil tank 42 to the first clutch 22 and to the second clutch 23. A pipe 44 can be branched off from the pipe 43 so as to feed the oil to various parts of the engine 10. Thus, the hydraulic system 40 serves both as a hydraulic system to control the twin clutch of the AMT 20 and as a hydraulic system to circulate and supply the oil to the engine 10.

The electric pump 41 is provided to the pipe 43 and the pipe 44 so that the oil in the oil tank 42 can be supplied both to the clutch side and to the engine side. The hydraulic pressure in each of the pipes 43 and 44 should be kept below a certain value. To this end, a return pipe 46 is provided so as to return the oil to the oil tank via a regulator 45.

The electric pump 41 can be configured so that the amount of the oil supply may be determined by changing the revolutions of the pump in accordance with the value of the driving current. A data measurement apparatus 47 capable of detecting the value of the driving current and the revolutions of the pump is attached to the electric pump 41.

A valve 55 is connected to the downstream side of the electric pump 41. The valve 55 includes two pressure chambers that make it possible to apply hydraulic pressure individually to the first clutch 22 and the second clutch 23. Additionally, return pipes 48 are connected respectively to the pressure chambers of the valve 55.

A return pipe 49 can be connected to the side of the engine 10, and allows the oil to be circulated in the engine 10 and supplied to the various parts of the engine.

An oil-temperature sensor 50 can be provided to detect the temperature of the oil and a hydraulic-pressure sensor 51 to detect the pressure of the oil are provided in the pipe 43. In the pipe 43, an oil filter 52 to clean the circulated oil is provided between the electric pump 41 and the hydraulic-pressure sensor 51.

An oil-amount detection sensor 53 can be provided to detect the amount of oil in the tank is provided on the bottom surface side of the oil tank 42. The oil-amount detection sensor can determine that an oil change has been done by detecting that the oil tank 42 has been emptied and then is filled again.

A mode switch 61 and a shift-selector switch 62 can be connected to the AMT control unit 60. The mode switch 61 is provided to switch between the automatic transmission (AT) and the manual transmission (MT). The shift-selector switch 62 designates either the up-shifting (UP) or the down-shifting (DN). In addition, the ATM control unit 60 receives information on the engine revolutions, the vehicle speed and the gear-shift position respectively obtained by the engine-revolution sensor 36, the vehicle-speed sensor 37, and the gear-position sensor 38 described above, information on the opening degree of the throttle obtained by a throttle sensor (not illustrated) provided on the throttle side, and the like.

The AMT control unit 60 includes a micro computer (CPU). The AMT control unit 60 operates following a predetermined procedure in response to the output signals from the above-mentioned various sensors and switches, and thus controls the valve 55 and the shift control motor 25. The AMT control unit 60 controls the first clutch 22 and the second clutch 23 in response to the driving states, such as the vehicle speed, the engine revolutions, the gear position, and the throttle opening degree so as to automatically switch the transmission gears of the AMT 20. Concurrently, the AMT control unit 60 determines the degradation of the oil by detecting the measured data on the electric-current value and the revolutions by the data measurement apparatus 47 of the electric pump 41 and by detecting the temperature of oil by the oil-temperature sensor 50 provided in the pipe 43.

In the above-described configuration, when the driving of the electric pump 41 applies hydraulic pressure to the valve 55 and raises the hydraulic pressure in the pipe 43 and the pipe 44, the oil flows out through the return pipe 46 while pressing a spring 45a of the regulator 45. Thereby, the hydraulic pressure is controlled so as not to exceed the upper limit value. Meanwhile, the upper limit values of the amount of oil supplied by the electric pump 41 and the pressure applied by the regulator 45 to return the oil to the return pipe 46 are set so that the hydraulic pressure in the pipe 43 and the pipe 44 may keep a value suitable to apply sufficient pressure to both of the valve control system and the engine lubrication system.

When the instruction given by the AMT control unit 60 makes the valve 55 open, the hydraulic pressure is applied either to the first clutch 22 or the second clutch 23, and the primary driven gear 32 is thus linked either to the inner main shaft 26a with the first clutch 22 or to the outer main shaft 26b with the second clutch 23. When the valve 55 is closed and the applying of the hydraulic pressure is stopped, the primary driven gear 32 is biased, by each of return springs (not illustrated) that are built respectively in the first clutch 22 and the second clutch 23, to a direction such that the link with the inner main shaft 26a or the outer main shaft 26b can be disconnected.

In response to the instruction given by the AMT control unit 60, the shift control motor 25 moves rotatably the shift drum 24. The rotational motion of the shift drum 24 moves the shift forks 29 following the shape of the cam groove formed in the outer circumference of the shift drum 24. The shift forks 29 thus moved is displaced in the axial direction of the shift drum 24, and moves the dog clutches to select a different set of gears on the counter shaft 27 and the main shaft 26. Thereby, the transmission gears 21 are either up-shifted or down-shifted.

When the mode switch 61 is switched to "AT," the AMT control unit 60 controls the first clutch 22 and the second clutch 23 in accordance with the driving conditions, such as the vehicle speed, the engine revolutions, the gear position, and the throttle opening degree so that the transmission gears 21 of the AMT 20 may be automatically up-shifted or down-shifted. When the mode switch 61 is switched to "MT," the transmission gears 21 are up-shifted or down-shifted with the first clutch 22 and the second clutch 23 being operated in accordance with the driver's up-shifting or down-shifting operation of the selector switch 62.

Next, the configuration of a part of the AMT control unit 60 related to the oil-degradation determination will be described with reference to a block diagram shown in FIG. 2.

The oil-degradation determination apparatus is an apparatus that determines the degradation of oil by measured data obtained by the data measurement apparatus 47 attached to the electric pump 41. The apparatus can include electric-current initial-value storing means or initial-value storing unit 1a which stores the electric-current initial value of the driving current for the electric pump 41. A pump-driving-time electric-current value measurement means or pump-driving-time data measurement unit 2a measures the electric-current value of the driving current for the electric pump 41. A comparison means or comparison unit 3 compares the electric-current initial value and the measured electric-current value. A determination means or determination unit 4 determines that the viscosity of the oil has become low when the difference between the electric-current values compared by the comparison unit 3 is equal to or more than a predetermined value.

The electric-current initial-value storing unit 1a can be, in a case where the oil-amount detection sensor 53 detects that the oil tank 42 has been emptied of the oil and then is filled again with new oil (i.e. after an oil change has been done), configured to measure the electric-current value of the driving current for the electric pump 41 by using the data measurement apparatus 47 when the engine 10 is driven, and to store the value thus obtained as the electric-current initial value.

The viscosity of oil becomes low when the oil is degraded, and thus the driving current of the electric pump 41 that is needed for the degraded oil to be circulated and supplied is lowered. Accordingly, the oil-degradation determination apparatus of this embodiment is configured to detect the change in the viscosity of oil by measuring the electric-current value of the above-mentioned driving current.

The electric-current value for the electric pump 41 is measured while the engine is running, the electric pump 41 is constantly rotating at a predetermined rate, and the temperature of the oil detected by the oil-temperature sensor 50 is at a predetermined temperature. A revolution detecting device is provided in the data measurement apparatus 47 installed in the electric pump 41 so as to detect whether the electric pump 41 is being driven to rotate at the predetermined rate.

The pump-driving-time electric-current value measurement unit 2a can be configured to collect data by measuring the electric-current value of the driving current of the electric pump 41 under conditions that the engine is being driven a predetermined time after the oil exchange, that the electric pump 41 is constantly rotating at the predetermined rate, and that the temperature of the oil is the same as that at the time when the electric-current initial value was measured. The revolution detecting device that is provided in the data measurement apparatus 47 installed in the electric pump 41 detects whether the electric pump 41 is being driven to rotate at the predetermined rate. Since the viscosity of oil sometimes varies with different temperatures, electric-current value is measured when the temperature of oil detected by the oil-temperature sensor 50 is the same as that at the time when the electric-current initial value was measured in order to detect more accurately the degrading state of the oil. In summary, factors that may influence the measured values of the electric-current initial value and the electric-current value of the electric pump 41 other than the degradation of the oil are precluded so that the degradation of the oil can be accurately reflected in the difference between the two electric-current values.

Further, the pump-driving-time electric-current value measurement unit 2a is configured to be capable of collecting the data at desired regular intervals. To implement the measurement at the desired regular intervals, the time elapsed after the change of the engine oil is managed by a built-in clock. Then, the data are collected, for example, at regular intervals set by the user or at regular intervals having been predetermined in advance (for example, for every ten days).

The comparison unit 3 is configured to compare the electric-current initial value stored in the electric-current initial-value storing unit 1a and the electric-current value measured by the pump-driving-time electric-current value measurement unit 2a.

When the difference between the electric-current values compared by the comparison unit 3 is equal to or larger than the predetermined value having been stored in advance, the determination unit 4 determines that the viscosity of the oil has been lowered. Then, the determination unit 4 outputs a signal to this effect to a warning device 5 connected to the determination unit 4. The warning device 5 includes a display for showing visually the information by using light-emitting elements, a liquid crystal, or the like that is provided in a meter 6.

The warning device 5 notifies the user of the degradation of the oil by lighting the display (monitor lamp) in the meter 6 in response to the signal thus received. Alternatively, the lighting of the display may be replaced by or used together with a sound generating device that generates a warning sound.

Still alternatively, the oil-degradation determination apparatus may be provided with data recording means that records pieces of data measured at regular intervals by the pump-driving-time electric-current value measurement unit 2a. These pieces of data stored in the data recording unit and the electric-current initial value stored in the electric-current initial-value storing unit 1a are respectively output to oil-change time calculating unit or means 7. The oil-change time calculating unit 7 calculates how long it will take for the oil to reach a degraded state that requires the changing of oil (i.e., when to change the oil) by using a function having been stored in advance and used for obtaining the time at which the oil will be degraded.

The user can be notified of the time of oil change thus calculated by displaying the information on a display device 8 in the meter 6.

The measured data stored in the data recording unit of the pump-driving-time electric-current value measurement unit 2a and the electric-current initial value recorded in the electric-current initial-value storing unit 1a are reset when the oil-amount detection sensor 53 detects that the oil tank is emptied of the oil.

Figure 3:
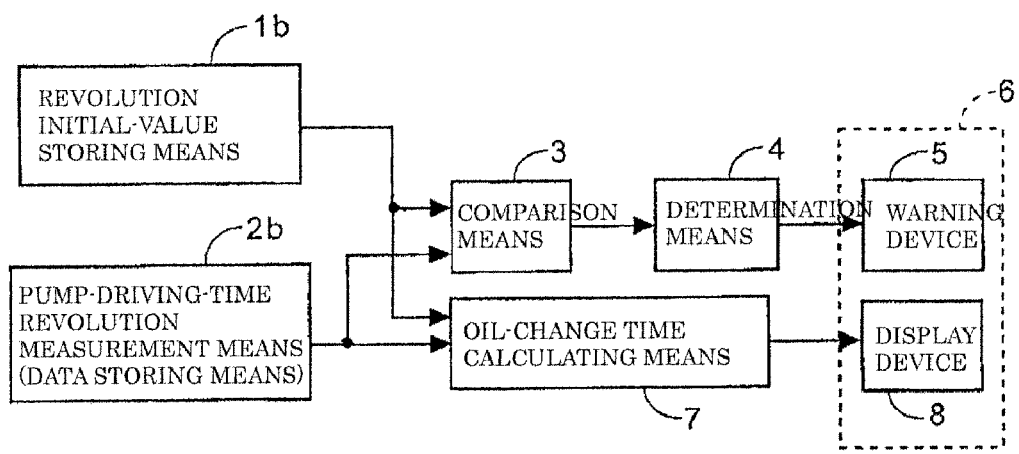
FIG. 3 is a general block diagram of an oil-degradation determination apparatus according to another embodiment of the present invention.

FIG. 3 is a general block diagram of an oil-degradation determination apparatus according to another embodiment of the present invention.

In summary, while the electric-current initial-value storing unit 1a stores the electric-current initial value of the driving current for the electric pump, and the pump-driving-time electric-current value measurement unit 2a measures the electric-current value of the driving current for the electric pump in the example shown in FIG. 2, these units of means are replaced with revolution initial-value storing unit or means 1b and pump-driving-time revolution measurement unit or means 2b in the example shown in FIG. 3. Note that parts that are common in the configurations shown in FIGS. 2 and 3 are given the identical reference numerals in the two drawings.

In a case where the oil-amount detection sensor 53 detects that the oil tank 42 has been emptied of oil and then is filled again with new oil (i.e. after an oil change has been done), when the engine is driven, the revolution initial-value storing unit 1b is configured to measure the revolution of the electric pump 41 under conditions that the electric pump is running with a predetermined electric current, and that the temperature of oil detected by the oil-temperature sensor 50 is at a predetermined temperature, and to store therein the revolution thus measured as a revolution initial value.

The pump-driving-time revolution measurement unit 2b is configured to collect data by measuring the revolution of the electric pump 41 under conditions that the electric pump 41 is running with the predetermined electric current, and that the temperature of oil detected by the oil-temperature sensor 50 is the same as that at the time when the revolution initial value was measured.

The viscosity of oil becomes low when the oil is degraded, and thus the revolution of the electric pump 41 that is needed to circulate and supply the degraded oil is increased. Accordingly, the oil-degradation determination apparatus of this embodiment is configured to detect the change in the viscosity of the oil by measuring the above-mentioned revolution.

The revolution of the electric pump 41 is measured, when the engine is driven, under the conditions that the value of the driving current for the electric pump 41 is kept constantly at the predetermined electric-current value, and that the temperature of oil detected by the oil-temperature sensor 50 is kept constantly at the predetermined temperature. This excludes factors other than the degradation of the oil from the factors that may influence the revolution initial value and the revolution measured value of the electric pump 41 with the pump being driven, so that the degradation of the oil can be accurately reflected in the difference between the two revolutions.

The comparison unit 3 is configured to compare the revolution initial value and the revolution measured with the pump being driven. When the difference between the revolutions compared by the comparison unit 3 is equal to or larger than a predetermined value, it is determined that the viscosity of the oil has become low.

An electric-current detecting device is provided in the data measurement apparatus 47 installed in the electric pump 41 so as to detect whether the driving current for the electric pump 41 is kept constantly at the predetermined electric-current value during the driving of the electric pump 41.

In the above-described embodiments, the electric pump 41 is configured to serve both as an electric pump for controlling the twin clutch and as an electric pump for circulating and supplying oil to the engine. Alternatively, two dedicated electric pumps may be respectively provided individually. In this case, the data measurement apparatus 47, which measures data to be outputted to the oil-degradation determination apparatus of the AMT control unit 60 and which serves both as the revolution detection device and the electric-current detection device, is provided on the side of the electric pump that circulates and supplies oil to the engine.

According to embodiments of the present invention, the detection of the degradation of the engine oil does not rely on a special sensor that is in contact with the oil. Instead, the degradation of the oil can be determined by detecting the state of oil through the comparison either between the measured electric-current value for the electric pump and its initial value or between the measured revolution of the electric pump and its initial value. Accordingly, it is not necessary to install a sensor to detect physical properties of the oil. Consequently, the oil-degradation determination apparatus can have a simpler structure and can be manufactured at a lower cost.

[Explanation of the Reference Numerals]
1a ELECTRIC-CURRENT INITIAL-VALUE STORING UNIT
1b REVOLUTION INITIAL-VALUE STORING UNIT
2a PUMP-DRIVING-TIME ELECTRIC-CURRENT VALUE MEASUREMENT UNIT
2b PUMP-DRIVING-TIME REVOLUTION MEASUREMENT UNIT
3 COMPARISON UNIT
4 DETERMINATION UNIT
5 WARNING DEVICE
7 OIL-CHANGE TIME CALCULATING UNIT
8 DISPLAY DEVICE
10 ENGINE
20 AUTOMATIC MANUAL TRANSMISSION (AMT)
21 TRANSMISSION GEARS
22 FIRST CLUTCH
23 SECOND CLUTCH
24 SHIFT DRUM
25 SHIFT CONTROL MOTOR
26 MAIN SHAFT
27 COUNTER SHAFT
28 TRANSMISSION-GEAR OUTPUT SHAFT
29 SHIFT FORKS
40 HYDRAULIC SYSTEM
41 ELECTRIC PUMP
47 DATA MEASUREMENT APPARATUS
50 OIL-TEMPERATURE SENSOR
55 VALVE
60 AMT CONTROL UNIT

We claim:

1. An oil-degradation determination apparatus, said apparatus comprising:
an initial-value storing unit configured to measure a first electric-current value of a driving current used to operate an electric oil pump at a predetermined constant revolution, said electric pump configured to circulate oil in an engine, said initial-value storing unit also being configured to store the first electric-current value as an electric-current initial value;
a pump-driving-time date measurement unit configured to correct data by measuring a second electric-current value of the driving current, said second electric-current value being measured when the electric pump is operated at the predetermined constant revolution when the engine is driven a predetermined time after the electric-current initial value is stored, wherein the pump-driving-time data measurement unit is configured to collect data at predetermined intervals;
a comparison unit configured to compare the electric-current initial value with the second electric-current value;
a determiner configured to determine that a viscosity of the oil has become low when it is determined that a difference between the electric-current initial value and the second electric-current value is equal to or greater than a predetermined value;
a data recording unit configured to record data measured at the predetermined intervals by the pump-driving-time data measurement unit; and
an oil-change time calculating unit configured to calculate, from the data stored in the data recording unit, an appropriate time for changing the oil.

2. The oil-degradation determination apparatus according to claim 1, further comprising:
a warning unit configured to display a visual warning or generate a sound warning, each warning indicating that the determiner has determined that the viscosity of the oil has become low.

3. The oil-degradation determination apparatus according to claim 1, wherein the initial-value storing unit is configured to measure and store the electric-current initial value immediately after a changing of the oil.

4. An oil-degradation determination apparatus, said apparatus comprising:
an initial-value storing means for measuring a first electric-current value of a driving current used to operate an electric oil pump at a predetermined constant revolution, said electric pump for circulating oil in an engine, said initial-value storing means also for storing the first electric-current value as an electric-current initial value;
a pump-driving-time date measurement means for correcting data by measuring a second electric-current value of the driving current, said second electric-current value being measured when the electric pump is operated at the predetermined constant revolution when the engine is driven a predetermined time after the electric-current initial value is stored, wherein the pump-driving-time data measurement means collects data at predetermined intervals;
a comparison means for comparing the electric-current initial value with the second electric-current value;
a determining means for determining that a viscosity of the oil has become low when it is determined that a difference between the electric-current initial value and the second electric-current value is equal to or greater than a predetermined value;
a data recording means for recording data measured at the predetermined intervals by the pump-driving-time data measurement means; and
an oil-change time calculating means for calculating, from the data stored in the data recording means, an appropriate time for changing the oil.

5. The oil-degradation determination apparatus according to claim 4, further comprising:
a warning means for displaying a visual warning or generating a sound warning, each warning indicating that the determining means has determined that the viscosity of the oil has become low.

6. The oil-degradation determination apparatus according to claim 4, wherein the initial-value storing means is also for measuring and storing the electric-current initial value immediately after a changing of the oil.

7. A method of determining oil-degradation, said method comprising:

measuring a first electric-current of a driving current used to operate an electric oil pump at a predetermined consistent revolution, said electric pump circulating oil in an engine;

storing the first electric-current value as an electric-current initial value;

measuring a second electric-current value of the driving current when the electric pump is operated at the predetermined consistent revolution when the engine is driven a predetermined time after the electric-current initial value is stored, wherein the measuring comprises collecting data at predetermined intervals;

comparing the electric-current initial value with the second electric-current value;

determining that a viscosity of the oil has become low when a difference between the electric-current initial value and the second electric-current value is equal to or greater than a predetermined value;

recording the data measured at the predetermined intervals; and calculating, from the data recorded, an appropriate time for changing the oil.

\* \* \* \* \*